(12) United States Patent
Butler et al.

(10) Patent No.: US 6,555,073 B1
(45) Date of Patent: *Apr. 29, 2003

(54) CATALYTIC REDUCTION OF PHENYLACETYLENE IN A STYRENE STREAM

(75) Inventors: James Roy Butler, Houston, TX (US); Kevin Peter Kelly, Friendswoods, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/932,415

(22) Filed: Aug. 19, 1992

Related U.S. Application Data

(63) Continuation of application No. 07/593,706, filed on Oct. 4, 1990, now abandoned.

(51) Int. Cl.[7] .............................. B01J 10/00; B01J 8/00; B01J 8/02; B01J 8/04
(52) U.S. Cl. ...................... 422/194; 422/171; 422/172; 422/177; 422/188; 422/189
(58) Field of Search .................. 422/224, 189–191, 422/193–194, 171, 177, 211, 213, 172; 366/336

(56) References Cited

U.S. PATENT DOCUMENTS

| | | | |
|---|---|---|---|
| 3,291,839 A | * 12/1966 | Carney et al. | 422/190 X |
| 3,468,641 A | * 9/1969 | Gross et al. | 422/190 X |
| 3,969,190 A | * 7/1976 | Hise et al. | 435/313 |
| 4,612,088 A | * 9/1986 | Nardi | 162/235 |
| 4,816,353 A | * 3/1989 | Wertheim et al. | 422/191 X |
| 5,156,816 A | * 10/1992 | Butler et al. | 422/141 |

OTHER PUBLICATIONS

Chemical Engineers Handbook, 5th Ed., R. H Perry, C. H. Chilton, 1973.*

* cited by examiner

*Primary Examiner*—Jerry D. Johnson
*Assistant Examiner*—Alexa A. Doroshoenk
(74) *Attorney, Agent, or Firm*—Bradley A. Misley

(57) ABSTRACT

Processes and apparatus are disclosed for the catalytic purification of styrene monomer by hydrogenating the phenylacetylene contaminant therein to styrene in a catalytic bed using multiple hydrogen injection; dilution of the hydrogen by a diluent such as nitrogen; mixing the hydrogen with a catalyst-selectivity improver such as carbon monoxide; using ethylbenzene dehydrogenation ventgas to supply hydrogen; and, using a multiple-catalyst-bed-reactor, or multiple reactors, each with a single catalyst bed. One preferred phenylacetylene reduction catalyst used is palladium on an alumina carrier.

4 Claims, 3 Drawing Sheets

CATALYTIC REDUCTION OF PHENYLACETYLENE IN A STYRENE STREAM

CROSS-REFERENCE TO RELATED APPLICATIONS

This application is a continuation of prior application Ser. No. 07/593,706, filed Oct. 4, 1990, for "CATALYTIC REDUCTION OF PHENYLACETYLENE IN A STYRENE STREAM."

FIELD OF THE INVENTION

The present invention relates to the field of monovinyl aromatic compound purification and polymerization, and more particularly discloses processes and apparatus for reduction the of phenylacetylene contaminants in crude styrene feedstock.

BACKGROUND OF THE INVENTION

Of all the thermoplastics manufactured today, probably the most versatile and most widely utilized class of materials is polymerized monovinyl aromatic compounds, such as polystyrene, polymerized alpha-methyl styrene, and polymers of ring-substituted styrenes.

Some of the most common uses of these compounds (often referred to collectively as "styrenes" or "polystyrenes") are for food and beverage containers, food wrap, and children's toys. One disadvantage associated with such uses of polystyrene is the residual monomer and other contaminants in the polymer which may contribute to off-taste, odor, off-color and other adulteration or degradation of the polymer.

A particularly offensive contaminant associated with such undesirable properties in polystyrene is unreacted vinyl aromatic monomer, usually styrene monomer. One of the causes of unreacted monomer is directly related to the presence of phenylacetylene in tile styrene feedstock going into the polymerization reactor system.

In the manufacture of monovinyl aromatic polymer compounds and more particularly in the manufacture of polystyrene, benzene is reacted with ethylene to form ethylbenzene. This molecular compound is then dehydrogenated in an EB Dehydro unit to form styrene monomer. The styrene monomer is then polymerized, usually in the presence of a polymerization initiator or catalyst, to form the final polystyrene raw material.

Unfortunately, phenylacetylene, one of the undesirable side products of the EB Dehydro unit, is formed when ethylbenzene is dehydrogenated one step too far. Consequently, the product stream from the Dehydro unit contains styrene, ethylbenzene, and traces of phenylacetylene. The ethylbenzene easily is removed by conventional processes, such as distillation, leaving styrene monomer and phenylacetylene. The removal of phenylacetylene cannot be accomplished by distillation and has heretofore been difficult and costly.

The presence of phenylacetylene in styrene monomer has undesirable consequences regardless of whether the method of polymerization utilized comprises anionic, or free-radical polymerization. During anionic polymerization, phenylacetylene which is slightly acidic, consumes a stoichiometric amount of catalyst, such as butyllithium, wherein one molecule of butyllithium is removed from the polymerization process by each molecule of phenylacetylene. This loss of catalyst can be costly and causes the concentration of catalyst to be difficult to control. This, in turn, causes the molecular weight of the polystyrene to be difficult to control and can result in an increase in the concentration of low molecular weight polymer and even unreacted styrene in the polystyrene.

During free-redical polymerization, the presence of phenylatetylene can have detrimental effects on chain length and polymerization rate, because it is a poor chain transfer agent. Consequently, in the manufacture of polystyrene beads, which are used to make expanded or "foamed" polystyrene, significant amounts of residual styrene are left in the bead.

Styrene is a suspected carcinogen and creates undesirable taste, odor, and health hazards, when present in small amounts in polystyrene.

Thus, the presence of phenylacetylene in styrene monomer has adverse effects on cost, control of the polymerization process, and purity of the resulting polystyrene. The presence of phenylacetylene in polystyrene also results in olefinic bonds in the backbone of the polymer which can increase cross-linking and cause more rapid oxidation of the polymer, both of which degrade the polymer.

In free-radical polymerization of styrene, as the concentration of styrene goes down during the polymerization process, the relative concentration of phenylacetylene naturally increases, and, since phenylacetylene acts as a polymerization inhibitor, the polymerization process is undesirably affected.

Catalytic attempts at reducing the phenylacetylene levels in styrene monomer streams have involved the injection of high levels of hydrogen gas into the monomer in an attempt to reduce the phenylacetylene to styrene. Any hydrogen added into the stream in stoichiometric excess of the phenylacetylene present also resulted in a significant conversion of styrene back to ethylbenzene, causing a lower styrene concentration and a lower conversion rate. Significant reductions in phenylacetylene were achieved only at the expense of styrene conversion to EB and resultant loss of styrene production.

SUMMARY OF THE INVENTION

The present invention discloses processes and apparatus which achieve a reduction in the phenylacetylene levels of monovinyl aromatic monomer feedstock in polymerization systems by the use of either a two-bed reactor to replace the single-bed reactors, or a pair of catalyst reactors, each bed or reactor having injection means for injecting hydrogen gas or a mixture of hydrogen gas and a diluent into the monomer reaction stream to reduce phenylacetylene to styrene.

DESCRIPTION OF THE PREFERRED EMBODIMENTS

Figure 1:
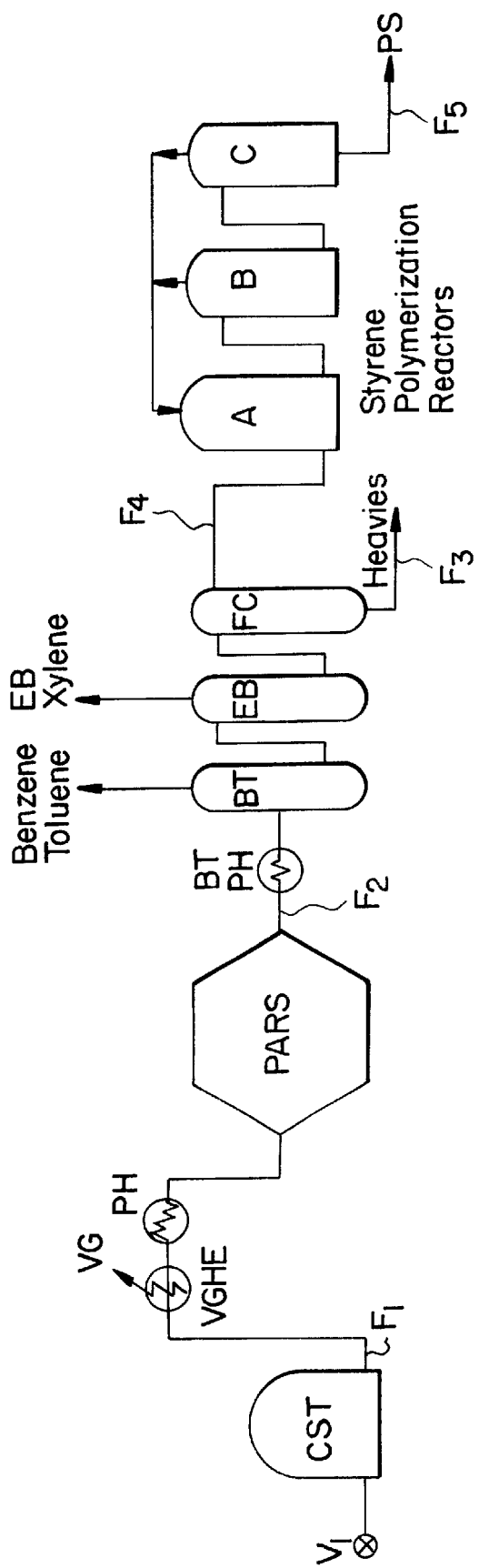
FIG. 1 comprises a simplified general schematic diagram of a typical monovinyl aromatic polymerization process utilizing the present invention.

Referring first to FIG. 1, this is a simplified schematic flow diagram representing a styrene purification and polymerization process. In FIG. 1, styrene monomer which has been created from the dehydrogenation of ethylbenzene is provided at valve V1 from where it flows into the crude styrene storage tank CST. From the storage tank crude styrene flows from flow line F1 through a vent gas heat exchanger VGHE to raise the temperature of the styrene, and from there into an optional preheater PH. From the preheater the crude styrene passes into the phenylacetylene reduction system PARS where the phenylacetylene in the crude styrene is reduced to acceptable levels. From the PARS, the refined crude styrene then flows through flow line F2 into the BT Column Preheater BTPH where the styrene temperature is raised prior to being injected into the BT Column. In this column, benzene and toluene are distilled off and removed through, the top. The refined styrene then passes into the EB Column where ethylbenzene and xylene are removed.

The other output from the EB Column contains the "heavies" and the refined styrene monomer. These are flowed into the Finishing Column FC where the heavies are separated from the purified styrene. The heavies are removed out flow line F3 and the purified styrene flows through line F4 into the styrene polymerization reactors A, B and C. The heavies removed from the finishing column include such things as pre-polymerized polystyrene indene, indane, and other heavies called "tars".

The styrene monomer is then polymerized in the three reactor polymerization system ABC and finished polystyrene is removed as indicated at PS through flow line F5. Columns B and C are shown having recycle lines exiting the top of the columns to recycle unpolymerized styrene monomer back into column A. As previously mentioned, this is a highly simplified schematic flow diagram of the polymerization process indicating one possible placement of the phenylacetylene reduction system of the present invention into a polystyrene system.

Figure 2:
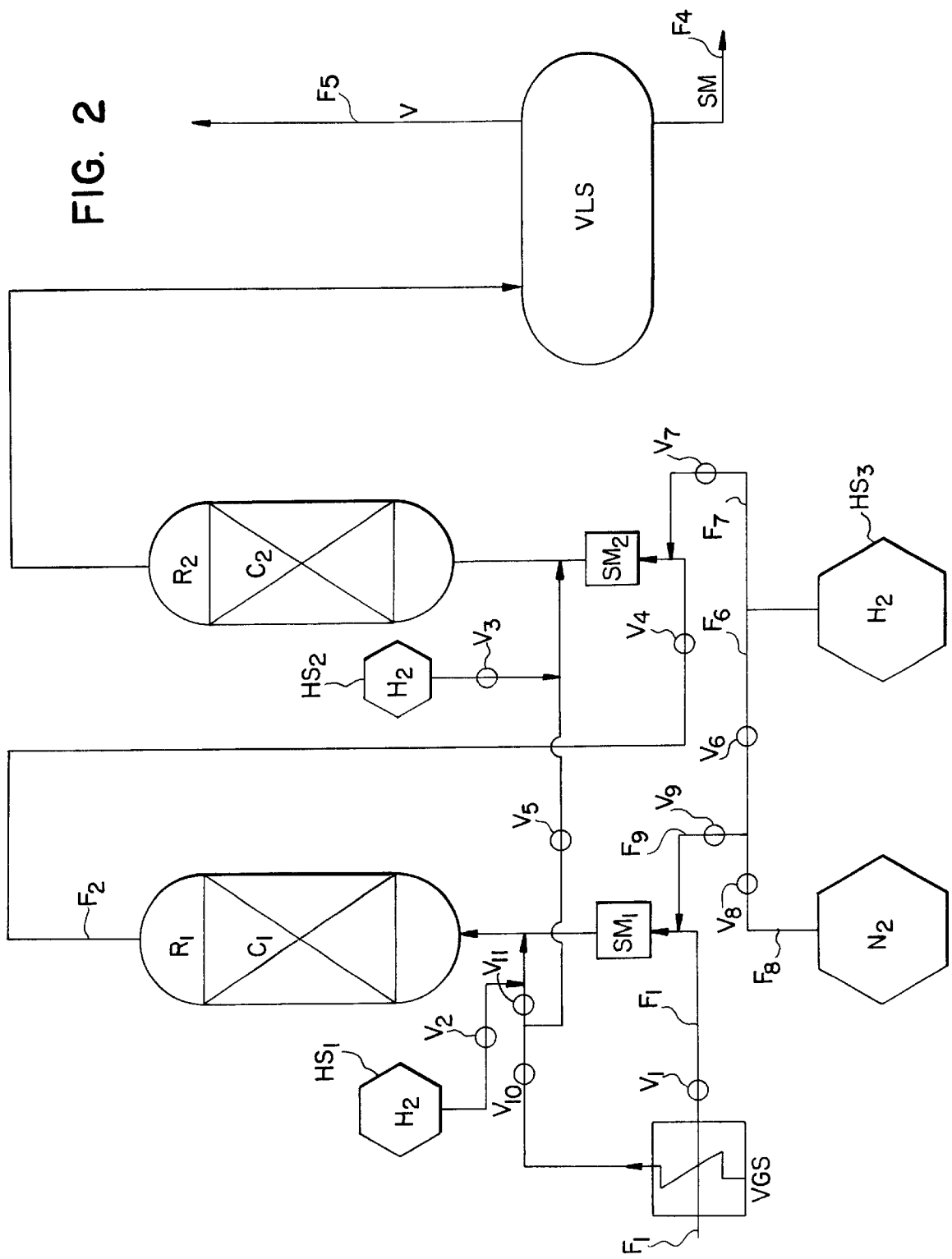
FIG. 2 is a partial schematic diagram of a two-reactor phenylacetylene reduction (PAR) system.

Referring now to FIG. 2, there are illustrated several embodiments of the phenylacetylene reduction system of the present invention. In FIG. 2, crude styrene flow line F1 leading from the crude styrene tank CST flows through the vent gas styrene heat exchanger VGS and is controlled by means of flow control valve V1 in line F1. From there crude styrene flows up through a static mixer SM1 and into the first reactor vessel R1 containing a catalyst bed C1 therein. Catalyst bed C1 may be of any type known in the art such as a fixed bed and preferably contains a spherical or lobed catalyst made up of about 0.3% palladium on an alumina carrier. In this embodiment the reactor vessel is preferably a liquid-full, upflow catalyst reactor.

The flow of crude styrene through the vent gas styrene heat exchanger serves two purposes, the first being that the styrene crude its brought up to a temperature of approximately 150° F. sufficient to initiate the phenylacetylene reduction process. The second purpose is to provide an optional vent gas supply to reactor R1 and reactor R2 to serve as a possible hydrogen source for hydrogen injection.

A source of hydrogen designated respectively HS1 and HS2 is provided for each reactor R1 and R2 and is controlled by valves V2 and V3. Alternatively, a single hydrogen source may be utilized such as a hydrogen supply pipeline, railroad or truck tank cars of hydrogen or even bottled hydrogen. Crude styrene then flows upward through catalyst bed C1 in reactor R1 and exits through flow line F2 which is connected via valve V4 to a second static mixer designated as SM2 and from there into the second reactor, R2 containing catalyst bed C2.

As previously mentioned, another source of hydrogen gas coming from the vent gas heat exchanger VGS is also supplied to reactors R1 and R2 via control valves V5, V10 and V11. From reactor R2 the purified styrene monomer stream flows via flow line F3 to the vapor liquid separator vessel designated VLS, wherein the purified styrene monomer stream designated SM exits via flow line F4. The separated vapors, designated V, exit through flow line F5 to be recycled in the process at the appropriate points. In addition to the hydrogen supplies indicated next to reactors R1 and R2, a third hydrogen source HS3 may be provided upstream of the static mixers to provide hydrogen via flow lines F6 and F7 through valves V6 and V7.

A supply of nitrogen designated N2 is provided in parallel with hydrogen source HS3, flowing nitrogen gas through flow line F8 and valve V8 to common line F9 controlled by valve V9. Optionally, hydrogen, or a mixture of nitrogen and hydrogen may be supplied to static mixer SM2 through flow line F7 and valve V7. Thus, a combination of hydrogen and nitrogen may be supplied to the crude styrene flow coming from the crude styrene tank via vent gas styrene heat exchanger VGS. The mixture of hydrogen and nitrogen is injected into the crude styrene and subjected to the action of static mixers SM1 and SM2 to provide a thorough mixture of the gases and the crude styrene feedstock. Preferably, a diluent gas is utilized with the ventgas hydrogen only in the first reactor bed, but can also be utilized if desired in both reactors.

Alternatively, rather than using a diluent gas, it has been found that the use of a catalyst modifier such as carbon monoxide (CO) can have beneficial results in PA reduction. It was an unexpected result that carbon monoxide acts in a synergistic manner with the hydrogen because CO normally acts as a "poison" to precious-metal catalysts. In the present instance, it was surprisingly found that the CO does not poison the catalyst but may, in fact, provide selectivity of hydrogenation towards the phenylacetylene and away from the styrene. It is believed that the CO does not permanently bond to the catalyst surface but instead, blocks those activation sites selective toward styrene while leaving available those sites active toward phenylacetylene. The change may involve changing the electronic configuration of the surface of the metal or the electronic environment thereon. CO is supplied to the PAR system in the EB dehydro ventgas in amounts less than about 1%, and preferably around 0.01 up to about 0.2%, but obviously can also be supplied by an independent source to be mixed with pure hydrogen.

In typical operation, crude styrene containing phenylacetylene contaminant is subjected to heat and its temperature raised to about 150° F. The heated crude styrene, containing high levels of phenylacetylene, is then subjected to a phenylacetylene reduction process by reacting hydrogen with the phenylacetylene in the presence of the palladium/alumina catalyst in at least two separate catalyst beds.

There are several alternative configurations of the phenylacetylene reduction process disclosed in FIG. 2. The first such system involves the injection of pure hydrogen into the crude styrene feedstock prior to its introduction into the reactor vessels. This may be achieved either prior to a static mixer by means of hydrogen source 3 through valves V6, V7, and V9, or may be accomplished without the static mixer through hydrogen sources HS1 and HS2 through valves V2 and V3. By manipulation of the various valves V1 through V11, pure hydrogen can be injected into the PAR process at the aforementioned points.

In addition to the reduction of phenylacetylene by means of pure hydrogen, an inert diluent may be utilized to control the reaction of styrene and hydrogen in the reactors to the point that very little styrene reduction and a high level of phenylacetylene reduction are achieved. One source of hydrogen which can be used involves vent gas from the EB dehydrogenation process which has been already used in heat exchanger VGS to preheat the crude styrene monomer prior to reaction in R1. The ventgas hydrogen can be combined with a pure diluent such as nitrogen gas supplied by means such as a nitrogen gas pipeline, railroad or truck tank cars; or even bottled nitrogen gas. A typical EB dehydro vent gas analysis indicates about 89% hydrogen, about 7% carbon dioxide, less than 1% carbon monoxide, and the remainder mostly hydrocarbons such as methane.

In a typical styrene monomer operation, the crude styrene feed into the PAR system would comprise about 60% styrene, about 39% ethylbenzene and somewhat less than 1% phenylacetylene. Generally measured levels of phenylacetylene in crude styrene range in the amounts up to about 250 parts per million (ppm). After reaction in the PAR system of the present invention, crude styrene feedstock having levels of phenylacetylene less than about 10 parts per million have been achieved and even levels in the range of 2 parts per million are believed achievable.

The purified styrene monomer is then flowed through flow line F3 to the vapor liquid separator VLS and the diluent gas and any possible remaining hydrogen gas are separated through vapor line V designated at F5 and the crude styrene feedstock comprising about 61% styrene and 39% ethylbenzene are flowed through the styrene monomer line designated F4 to the BT column as indicated in FIG. 1 where traces of benzene and toluene are separated from the feedstock. The ethylbenzene is then removed from the styrene in the EB column downstream of the BT column and the final refining step of the styrene monomer is accomplished in the finishing column designated FC.

Thus the inventive process as described with respect to FIG. 2 involves the use of either pure hydrogen as a reducing agent, hydrogen provided by means of EB vent gas, hydrogen mixed with a nitrogen diluent, or the use of hydrogen and carbon monoxide wherein the CO acts as a catalyst modifier to decrease the selectivity of the catalyst from reduction of styrene and to increase its selectivity toward the reduction of phenylacetylene. The ratio of $N_2$ to $H_2$ should be in the range of from 1:2 to 4:1, preferably about 1:1, diluent to hydrogen. The levels of carbon monoxide are preferably about 1000 to 2000 ppm, preferably about 1700 ppm.

Figure 3:
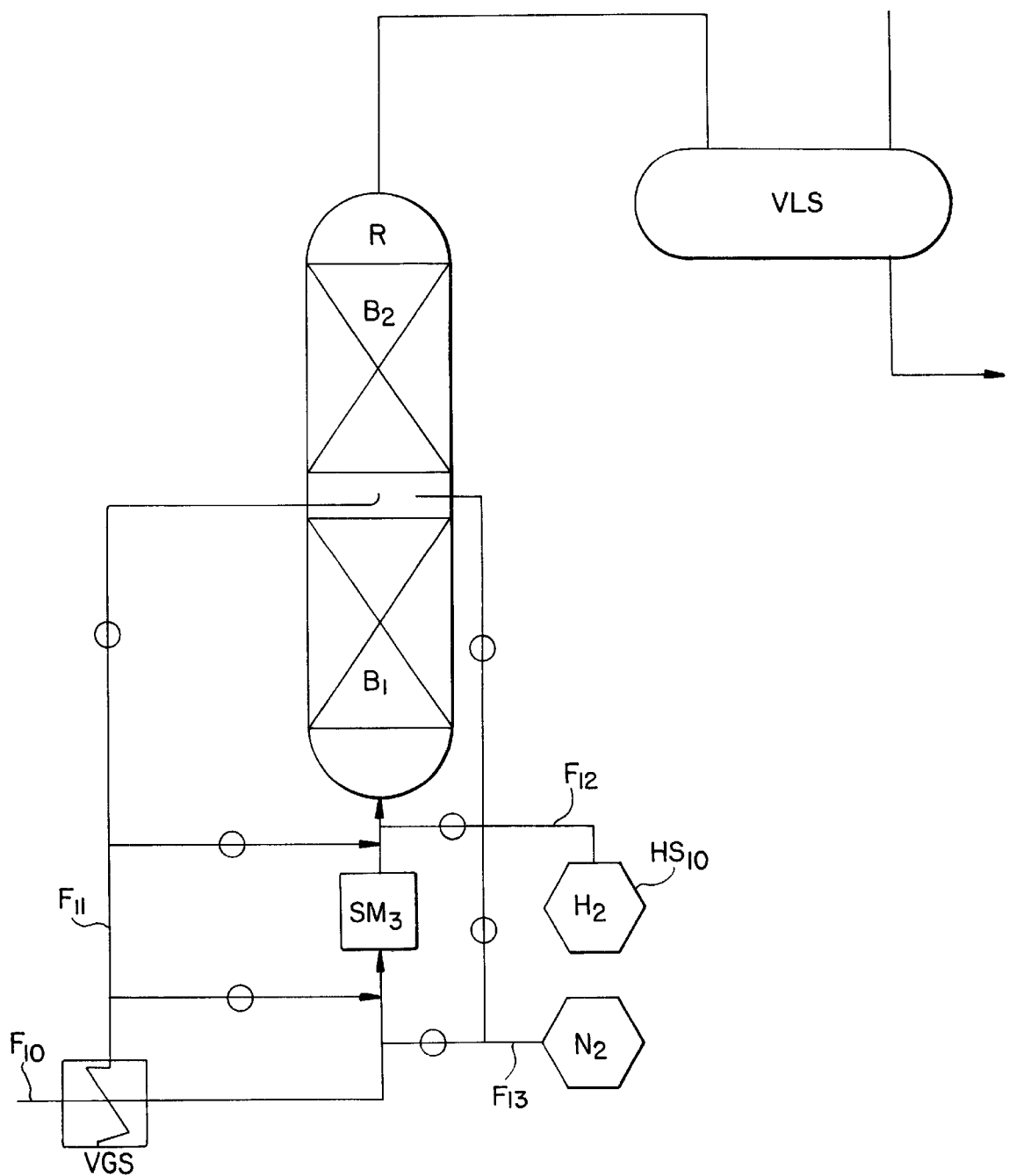
FIG. 3 is a partial schematic diagram of a two-bed single reactor PAR system.

FIG. 3 indicates yet another embodiment of the present invention in which the two reactors R1 and R2 of FIG. 2 have been replaced with a single two-bed reactor having catalyst beds B1 and B2 comprising either spherical or lobed catalyst of an alumina carrier with a palladium, metal. One particular catalyst which has been advantageous is that manufactured by Criterion Catalyst of Houston containing approximately 0.3% by weight palladium on an alumina carrier and designated as Criterion 05PAS.

Other catalysts and catalyst geometries might also be utilized; for example, palladium on a silica carrier, or extruded cylindrical pellets rather than spherical. In fact, it is possible that other known hydrogenation catalysts might be successfully utilized in the present invention. Of particular interest are the metals of Groups VIIB and VIII, the transition metals, including platinum, nickel, iridium, ruthenium, rhodium, osmium, rhenium and possibly even others. Other possibilities include these transition metals modified with Group IB and IIB metals such as gold, copper, and zinc. In addition to alumina and silica carriers, other known carriers might be utilized such as sodium alumino silicates. Alternatively, effective amounts of the catalyst metal could exceed or even greatly exceed the small amounts cited herein. Metal contents exceeding 1% and even 5% could possibly be utilized with this invention.

In FIG. 3, crude styrene enters through flow line F10 passing through vent gas styrene heat exchanger VGS and into static mixer designated SM3. From there the styrene flows into the reactor R passing first through catalyst bed B1 and then through catalyst bed B2. Vent gas from vent gas heat exchanger VGS is provided via flow line F11 through various valve means into three points in the PAR system, one point being prior to static mixer SM3, the second point being downstream of static mixer SM3 and the third point being in the central area of the reactor R between catalyst beds B1 and B2.

Hydrogen from hydrogen source HS10 may be supplied by flow line F12 and can be mixed with either carbon monoxide from a CO source, or with nitrogen from nitrogen source N2 through flow line F13 or it may be injected directly into the reactor either upstream or downstream of static mixer SM3, or in the central area of reactor R, by manipulation of the various valves in the various flow lines.

Thus, the options with the two-bed reactor of FIG. 3 are basically the same as those options in the two reactor system of FIG. 2, i.e., either pure hydrogen may be injected into the crude styrene prior to the static mixer, downstream of the static mixer, and/or in the central area of the reactor between the two reactor beds; or alternatively, hydrogen may be combined with an inert diluent, and this gas mixture injected either prior to or after the static mixer SM3 as well as in the central area of reactor R between beds B1 and B2. Likewise, hydrogen may be supplied by vent gas and optionally can be mixed with the diluent and injected at the same injection points mentioned above. As an additional option, hydrogen from any source may be mixed with carbon monoxide to increase the catalyst selectivity to phenylacetylene reduction, and injected into the reactor of FIG. 3 as described above.

Thus from the description set forth above with respect to FIGS. 1, 2 and 3, it can be seen that the embodiments of the present invention teach and disclose methods and apparatus for the reduction of the undesirable phenylacetylene contaminant in a stream of styrene monomer. This invention functions primarily by the addition of hydrogen to reduce phenylacetylene to styrene but implies several modifications such that the styrene is not reacted immediately upon contact with the catalyst in the PAR reactors. These methods of preventing reduction of styrene and phenylacetylene to ethylbenzene involve the use of multiple injection points, either by utilizing two reactors or by utilizing a two-bed single reactor. Further apparatus and processes of the present invention utilize the use of diluents comprising inert gases to slow the contact of hydrogen with the styrene monomer stream constituents. One particularly advantageous diluent disclosed is nitrogen. In addition, it is contemplated that a diluent such as fuel gas might also be advantageously used with the present inventive process. Other embodiments use a hydrogen gas combined with a catalyst modifier such as carbon monoxide to increase the selectivity toward phenylacetylene reduction.

Actual models utilizing the processes and apparatus of the invention have successfully reduced phenylacetylene levels in styrene monomer streams from an undesirable level of up to 250 parts per million down to highly desirable levels below 10 parts per million. Although not entirely sure of the exact mechanism and the reason for such a high success ratio with the present invention, we feel that it is probably due to a combination of the chemistry involved as well as the geometry of the catalyst which allows the hydrogen and the phenylacetylene to come together to react. It was also found that the present invention reduces the energy needed to start the phenylacetylene reduction and can primarily be accomplished with just the inherent heat content of the styrene feed at 150° F. from the VGS heat exchanger.

In practicing the process of this invention it was found that for reducing phenylacetylene levels of around 200 ppm, a desirable flow rate through the reactor system was about 30 LHSV. In addition, a hydrogen to phenylacetylene ratio of about 16 to 1 was found to provide good phenylacetylene reduction. The reactor pressure was operated at about 60 to 70 PSI inlet pressure. In the case of the two-reactor system, with an initial phenylacetylene concentration of about 200 ppm, 16 to 1 hydrogen to phenylacetylene ratio was split equally between each reactor. Likewise, in the two-bed reactor system with the dual injection locations, a 16 to 1 ratio of hydrogen to phenylacetylene was split equally between the two points. Although other ratios of hydrogen to phenylacetylene could be utilized successfully, it was found that this particular ratio provided good phenylacetylene reduction and low conversion of styrene back to ethylbenzene. The provision of hydrogen by using the vent gas from the EB Dehydro unit was a distinct advantage because of its ready availability.

In addition to these process conditions, various space velocities were measured through the reactor to determine the effect that space velocity had on phenylacetylene reduction and hydrogen consumption. It was determined that in the particular embodiments herein disclosed, the LHSV through the reactors had relatively little effect on the efficiency of the process.

For example, an effective upper limit on LHSV for long catalyst life was found to be about 60 overall. LHSV's of up to 240 were found to work in reducing phenylacetylene, but preferred rates were in the range of 30 to 120 LHSV, because the higher rates are believed to contribute to shorter catalyst life. An overall rate of 30 LHSV was found preferable in one embodiment.

Also the amount of styrene reduction, which is undesirable, was found to be only about 0.1% to 0.2% of the styrene being processed. Because of the nature of the styrene/polystyrene process, the conversion of styrene to ethylbenzene is not as detrimental to the process as the presence of phenylacetylene, since ethylbenzene is removed from the styrene monomer and recycled back into the dehydrogenation process to be converted back into styrene. The 0.1% to 0.2% loss of styrene through reduction to ethylbenzene is negligible and very acceptable. By the use of the multi-bed reactor, lessor amounts of hydrogen can be used such that the loss of styrene through reduction drops all the way to less than about 0.1% and phenylacetylene can be reduced to less than 30 parts per million.

Although a specific preferred embodiment of the present invention has been described in the detailed description and drawings above, the description is not intended to limit the invention to the particular forms or embodiments disclosed therein since they are to be recognized as illustrative rather than restrictive, and it would be obvious to those skilled in the art that the invention is not so limited. Thus the invention is declared to cover all changes and modifications of the specific examples of the invention herein disclosed for purposes of illustration which do not constitute departure from the spirit and scope of the invention.

The embodiments of the invention in which an exclusive property or privilege is claimed are defined as follows:

1. A system for the selective reduction of phenylacetylene to styrene in a styrene stream contaminated with phenylacetylene, said system comprising:

a single reactor vessel having a flow inlet at one end and a flow outlet at the other end;

a first reduction catalyst bed in said reactor vessel near the flow inlet;

a hydrogen injector upstream of said first catalyst bed arranged to inject hydrogen into said styrene stream;

a second reduction catalyst bed in said reactor vessel downstream from said first catalyst bed and near said flow outlet; and, a second hydrogen injector in said reactor vessel between said two catalyst beds.

2. The phenylacetylene reduction system of claim 1 wherein at least one of said catalyst beds has spherical alumina catalyst pellets with less than one percent weight palladium metal thereon.

3. A system for the reduction of phenylacetylene in styrene, said system comprising:

a first reactor vessel having a flow inlet, a flow outlet, and a reduction catalyst bed therein;

a second reactor vessel having a flow inlet communicating with the flow outlet of said first vessel, and further having a reduction catalyst bed therein;

a first hydrogen injector for injecting hydrogen into said first reactor vessel upstream of said catalyst bed therein;

a second hydrogen injector for injecting hydrogen into said second reactor vessel upstream of said catalyst bed therein; and a diluent injector associated with at least one of said hydrogen injectors and arranged to add a diluent gas to said hydrogen prior to injection into said vessel.

4. The system of claim 3 further comprising at least one static mixer upstream of at least one of said reactor vessels for mixing hydrogen, diluent gas, and styrene monomer prior to their entering said vessel.

* * * * *